United States Patent [19]

Carlson et al.

[11] 4,183,360
[45] Jan. 15, 1980

[54] MULTIFINGER PHOTOCELL PLETHYSMOGRAPHY SYSTEM

[75] Inventors: Walter Carlson; Donald Wasserman, both of Cincinnati; William Asburry, Bethel, all of Ohio

[73] Assignee: The United States of America as represented by the Department of Health, Education and Welfare, Washington, D.C.

[21] Appl. No.: 928,155

[22] Filed: Jul. 26, 1978

[51] Int. Cl.$^2$ ............................................. A61B 5/02
[52] U.S. Cl. ...................................... 128/666; 356/39
[58] Field of Search ............................... 128/665–667, 128/699, 633, 644; 356/39, 40, 42

[56] References Cited

U.S. PATENT DOCUMENTS

| | | | |
|---|---|---|---|
| 3,103,214 | 9/1963 | Smith | 128/666 |
| 3,450,133 | 6/1969 | Birch, Jr. | 128/644 |
| 3,623,473 | 11/1971 | Andersen | 128/691 |
| 3,628,525 | 12/1971 | Polanyi | 128/633 |
| 3,858,574 | 1/1975 | Page | 128/666 |
| 3,980,075 | 9/1976 | Heule | 128/666 |
| 3,998,550 | 12/1976 | Konishi et al. | 356/39 |
| 4,015,595 | 4/1977 | Benjamin, Jr. | 128/666 |

Primary Examiner—Kyle L. Howell
Attorney, Agent, or Firm—Browdy and Neimark

[57] ABSTRACT

A photoplethysmographic instrument for simultaneous recordings of multifinger blood flow. The instrument consists of a plurality of suitably spaced and angled finger-receiving housings, each containing a photodetector, with respective light pipe bundles conducting light from a common source to the housings. The photodetectors respond to differences in light transmission through the patient's fingers inserted in the housings. The photodetectors are connected through respective preamplifiers to the respective inputs of a multichannel recorder, thereby providing recorded traces of the respective optical transmissions through the fingers. The photodetectors may also be connected to the respective inputs of a multichannel tape recorder, thereby providing magnetic tape recordings of the respective optical transmissions.

15 Claims, 7 Drawing Figures

FINGER SWITCHING NETWORK

MULTIFINGER PHOTOCELL PLETHYSMOGRAPHY SYSTEM

FIELD OF THE INVENTION

This invention relates to photoplethysmograph devices, namely, devices for the measurement of peripheral pulsatile blood flow, and more particularly to a system for the simultaneous measurement and recording of the pulsatile blood flow through all the fingers of a patient's hand for the purpose of studying Raynaud's Phenomenon, also known as "vibration white fingers syndrome (VWF)".

BACKGROUND OF THE INVENTION

For many years, plethysmography has been used as a laboratory method for the assessment of the integrity of the vascular bed of the limbs by observing changes in peripheral blood volume. Within the last few years, the technique of using photoplethysmography has developed considerably. The technique involves the use of an optical source (usually an incandescent lamp) and an appropriate detector, and is theoretically based on the large difference between the extinction coefficients of blood and the body tissues. (See "Photoplethysmography" by J. Weiman, Manual of Psychophysiological Methods, North Holland Publ. Co., Amsterdam, Holland, 1967). The region of 7000-9000 A appears to be optimum for optical transmission through tissue and blood with large differences in optical transparency of tissue and blood. At 8050 A for example, Kramer ("Influence of Oxygen Saturation, Erythrocite Concentration and Optical Depth, Upon the Red and Near Infrared Regions", Kramer, K., Elam, J. O., Saxton, G. A., and Elam, W. N., Amer. J. Physiol. 165, pp. 229-246, 1951) has stated that normal whole blood layer of 1.3 mm thickness would transmit 0.7% of incident light; a similar tissue layer would yield a value of 62%.

In attempting to assess Raynoud's Phenomenon of occupational origin (also known as vibration white fingers syndrome (VWF), Taylor and others ("Proceedings of the International Occupational Hand-Arm Vibration Conference", edited by Wasserman, D., Taylor, W., and Curry, M., DHEW (NIOSH) Publication No. 77-170, April, 1977) have stated that there presently does not exist a single comprehensive and reliable test for assessing VWF in either the clinical or field situation. In a recently conducted laboratory study, these authors have successfully used single channel photoplethysmography as a tentative means of distinguishing between the peripheral circulation of normal human subjects and diagnosed Raynaud's disease patients.

A preliminary search has revealed the following prior patents which appear to show the state of the art:
Smith, U.S. Pat. No. 3,103,214
Planyi et al, U.S. Pat. No. 3,628,525
Page, U.S. Pat. No. 3,841,314
Heule, U.S. Pat. No. 3,980,075
Kenoshi et al, U.S. Pat. No. 3,998,550
Benjamin, U.S. Pat. No. 4,015,595

SUMMARY OF THE INVENTION

Since there are some 1.2 million workers in the United States exposed to hand-arm vibration who are potential candidates for VWF (see "Industrial Vibration—An Overview", Wasserman, D., Badger, D., Doyle, T., and Margolies, L., ASSE Journal, 19, 6, pp 38-43, 1974), a main object of the present invention is to provide an improved system for assessing VWF which overcomes the deficiencies and shortcomings of the methods and apparatus previously employed for this purpose. The improved system of the present invention particularly is intended for the simultaneous multifinger qualitative measurement of the vascular bed of the digits by the use of photoplethysmography, as distinguished from single-finger previously used systems.

Accordingly, a further object of the invention is to provide a method and apparatus for performing simultaneous multifinger photoplethysmography which employs relatively simple equipment, which is highly versatile, which employs durable components, and which constitutes reliable instrumentation for testing simultaneous changes in the peripheral circulation of the fingers.

A still further object of the invention is to provide an improved photoplethysmographic instrument for obtaining simultaneous recordings of multifinger blood flow, the instrument employing optical test housings with a common light source and individual photosensors for simultaneously receiving all the fingers of a patient's hand, the housings being individually adjustable in geometric orientation so as to be adaptable to various lengths an directions of the fingers of the hand as may occur with different individual patients.

A still further object of the invention is to provide an improved multifinger photoplethysmographic instrument for simultaneously qualitatively measuring the vascular bed of the digits and for providing simultaneous visible record traces of the pulsatile blood flow of the fingers, as well as simultaneous magnetic tape recordings of such flow.

Further objects and advantages of the invention will become apparent from the following description and claims, and from the accompanying drawings, wherein:

DESCRIPTION OF A PREFERRED EMBODIMENT

Figure 1:
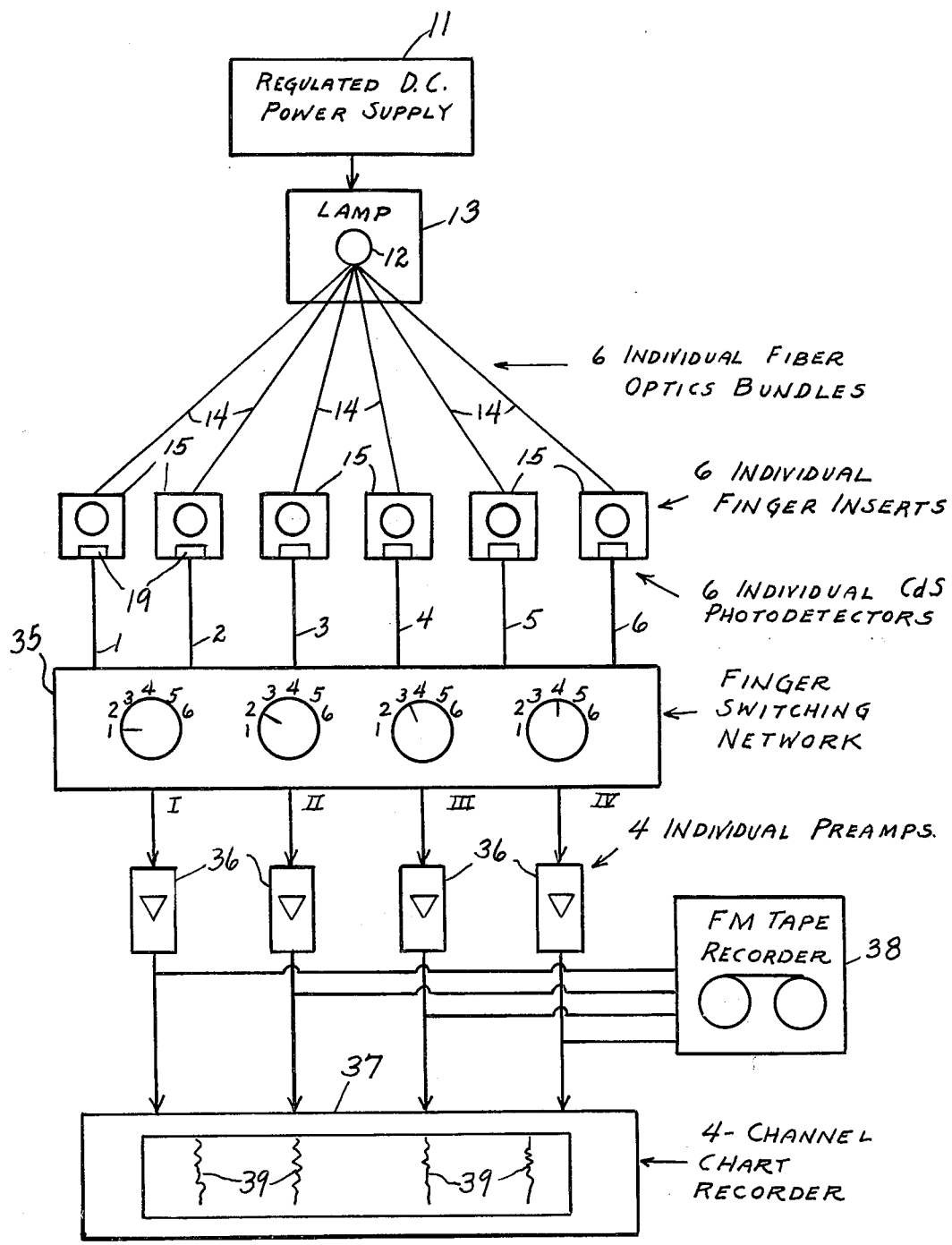
FIG. 1 is a block diagram of a multifinger photoplethysmographic system constructed in accordance with the present invention.

Referring to the drawings, and more particularly to FIG. 1, a regulated D.C. power supply 11, such as Power Designs Model 4010, supplies highly regulated 10 VDC to a single Type No. 1816 incandescent lamp 12 suitably mounted in an aluminum box 13. Six individual fiber optics bundles 14, such as Olson Model XM086, each about 12 inches in length, are suitably connected to box 13 so that they are simultaneously exposed at their upper ends, as viewed in FIG. 1, to a common limited light-emitting area of lamp 12. Each bundle 14 then separately transmits light to each of six finger insertion housings 15.

Figure 4:
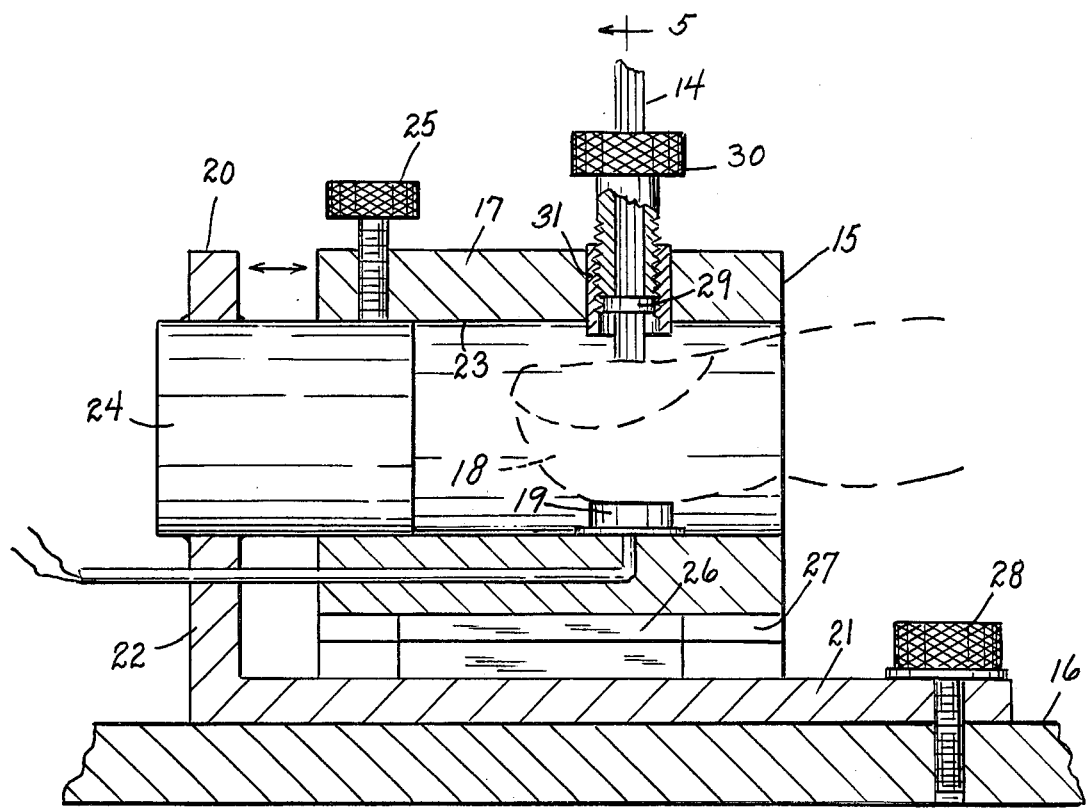
FIG. 4 is an enlarged vertical cross-sectional view taken through a finger-receiving housing substantially on the line 4—4 of FIG. 3.
Figure 6:
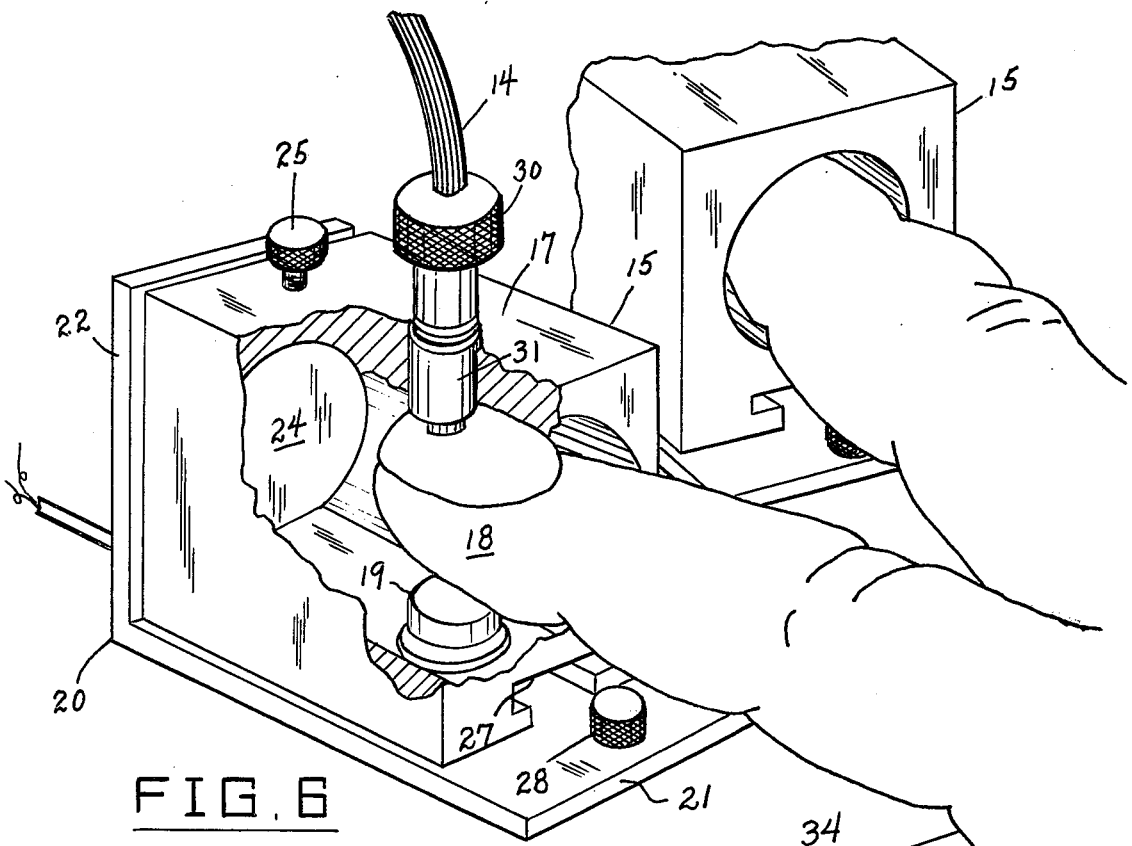
FIG. 6 is a perspective fragmentary view showing how an adjacent pair of a patient's fingers are received in optical test housings in the system of FIGS. 1 to 5.

Each finger insertion housing 15 is made of suitable opaque material, such as Delrin, and is adjustably mounted, in a manner presently to be described, on a common plate member 16, which may comprise any suitable material, such as acrylic plastic material, so that it can be adjusted to accommodate virtually any finger. There are six finger insertion housings 15 so as to accommodate either thumb at one or the other end of the housing array, and the remaining four fingers, depending on the hand under test, with a single fiber optics bundle 14 adjustably affixed through the top wall 17 of each finger insertion housing 15. Each fiber optics bundle 14 carries "cold light" to the tip of the distal phalange 18 of a finger inserted in the associated housing, thus eliminating localized tissue heating. Axially aligned with and located below each fiber optics bundle 14 is mounted a cadmium sulfide photodetector 19, such as Clairex Model No. CL707L. Each finger is placed between a fiber optics bundle 14 carrying light to the finger and the photodetector 19 below the finger, as shown in FIGS. 4 and 6. The use of a single light source guarantees uniformity of light intensity for each channel. If any light fluctuation should occur, it will occur simultaneously on all channels.

Figure 3:
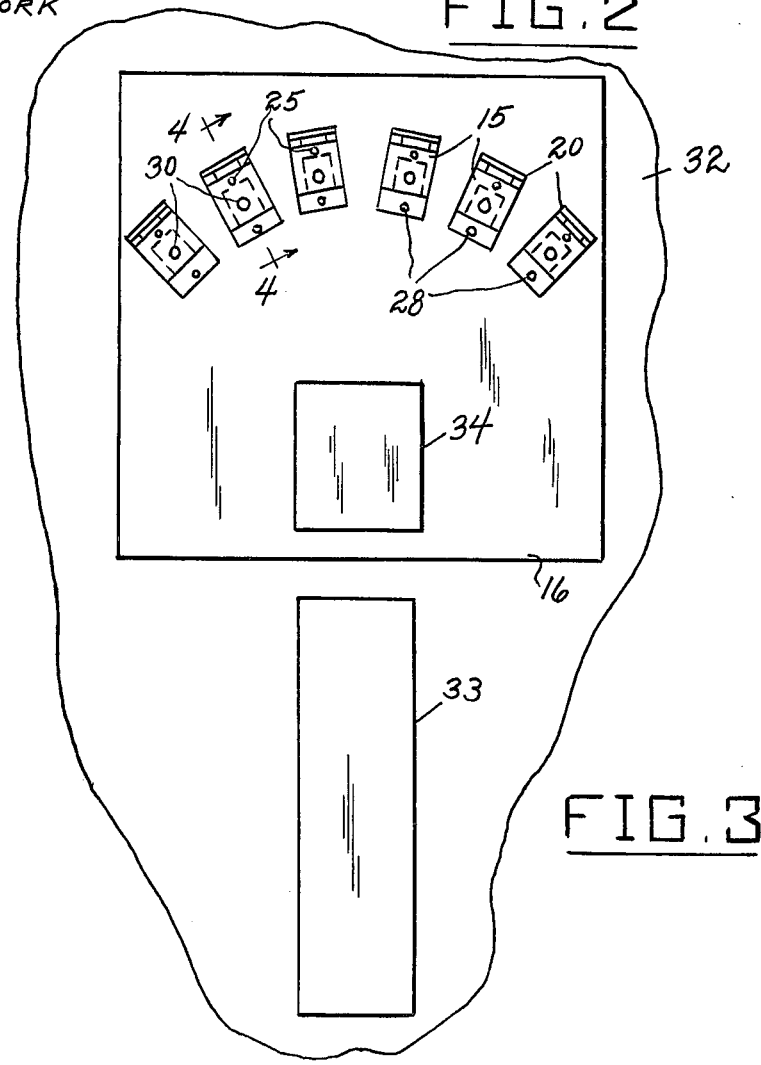
FIG. 3 is a top plan view showing a physical finger-receiving housing arrangement forming part of a multifinger photoplethysmographic instrument in the system of FIG. 1.
Figure 5:
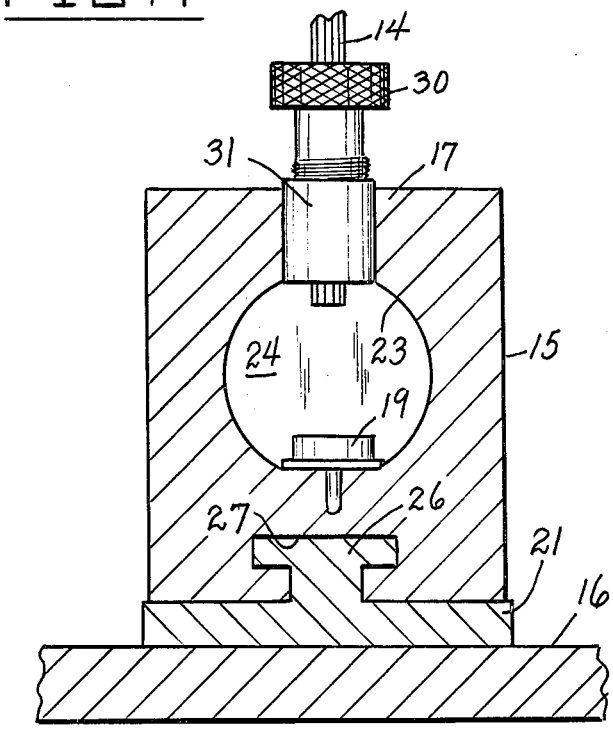
FIG. 5 is a transverse vertical cross-sectional view taken substantially on line 5—5 of FIG. 4.

Referring to FIGS. 3–5, each housing 15 may be supported on a bracket member or carriage 20 comprising a base plate 21 and an upstanding vertical flange 22. The housing 15 has a finger-receiving horizontal bore 23 telescopically engaged on a substantially cylindrical horizontal stud or boss 24 rigidly secured to flange 22. The top wall 17 of the housing is provided with a thumbscrew 25 clampingly engageable with boss 24 to lock the housing 15 in longitudinally adjusted position on bracket 20. Base plate 21 may be provided with an upstanding T-shaped longitudinal guide rib 26 slidably engaged in a T-shaped longitudinal groove 27 formed in the bottom portion of housing 15.

Base plate 21 may be pivotally connected to bottom plate member 16 by a clamping thumbscrew 28, which when loosened, allows bracket 20 to be pivotally adjusted horizontally, and which locks the bracket in angularly adjusted position when tightened.

Thus, the housing 15 may be adjusted longitudinally on bracket 20 and angularly in a horizontal plane around the pivot thumbscrew 28.

The associated light-admitting fiber bundle end portion is provided with an abutment collar 29 engaged by a thumbscrew bushing 30 surrounding bundle 14 above the collar and threadedly engaging in a fixed bushing member 31 rigidly secured in the top wall 17, as shown in FIG. 4. The fiber bundle end may be urged against the inserted finger by tightening the thumbscrew bushing 30 against the collar 29.

The base plate 16 may be mounted on a wood base 32, with an associated arm rest plate 33 secured forwardly adjacent the plate 16, as shown in FIG. 3. A flat copper palm rest plate 34, which is electrically grounded, is bonded to the plate 16. The patient's arm is placed on arm rest 33 and the palm of the hand is placed on grounded plate 34, the fingers being inserted in the appropriate finger insert housing bores 23. In order to accommodate different finger lengths, each finger insertion housing 15 can be individually adjusted longitudinally, as above described, and locked. The carriage bracket 20 of each finger insertion housing can be rotationally adjusted, as above described, and locked, in order to accommodate each finger at its proper angle as the hand rests on the palm plate 34. Finally, the fiber optics bundle can be brought down snugly to each finger by means of the thumbscrew bushings 30 so as to be held against movement. Thus, the assembly allows for varied ranges of anthropometric differences in human hands and insures uniform plethysmographic results for all fingers.

The six photodetectors 19 are selectively connected through a finger switching network 35 to four readout channels via the four individual preamplifiers 36. The four readout channels supply respective output signals to a 4-channel strip chart recorder 37, such as Brush Model 440, and to a portable 4-channel Instrumentation Tape Recorder 38, such as TEAC Model R-70-A. As shown in FIG. 1, the strip chart recorder 37 provides 4 recorded light transmission intensity traces 39, one for each of four selected fingers.

Figure 2:
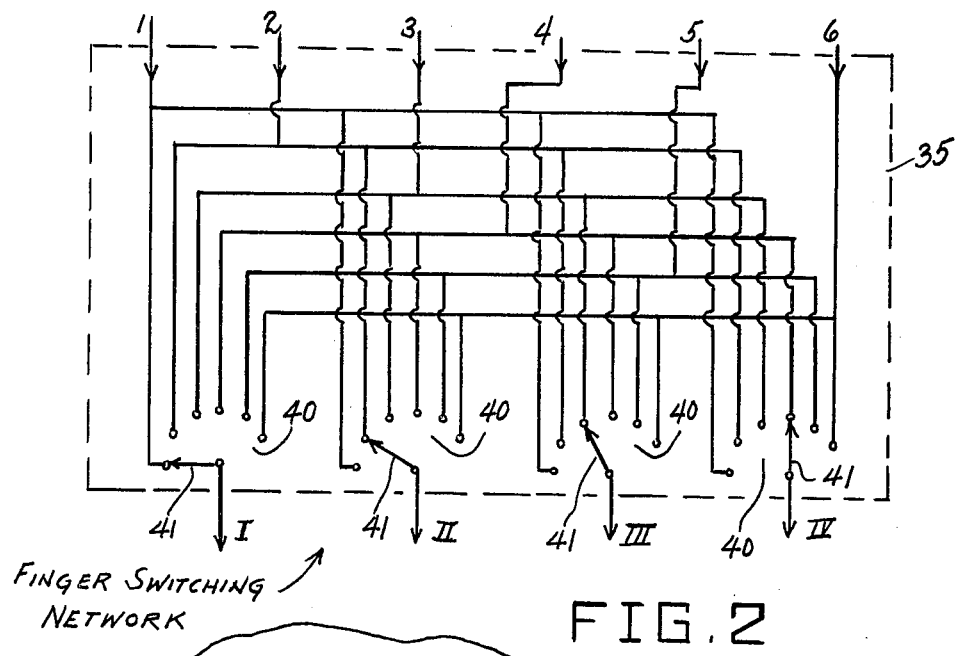
FIG. 2 is a wiring diagram of the finger switching network employed in the multifinger instrument system of FIG. 1.

The output wires 1 to 6 of the six photodetectors 19 are routed to four six-position rotary switches 40 in network 35, as shown in FIG. 2. The 6 output wires are each respectively connected to the 6 stationary contacts of the rotary switches, and the poles of the switches, shown at 41, are connected to the inputs of the respective preamplifiers 36. The rotary switches may be operated to select four respective fingers for readout. Thus, the effective output of each of the six photodetectors 19 is routed to the four 6-position rotary switches 40 which can be programmed to choose any of these effective photodetector outputs for signal preamplification and conditioning. After conditioning and preamplification have taken place, the amplified photoplethysmographic outputs are simultaneously presented to the portable 4-channel tape recorder 38 and the 4-channel strip chart recorder 37 for visual display. Thus, both a hard copy record of the multichannel plethysmogram is available, as well as a magnetic tape record for later data processing into a true RMS voltmeter averager.

Figure 7:
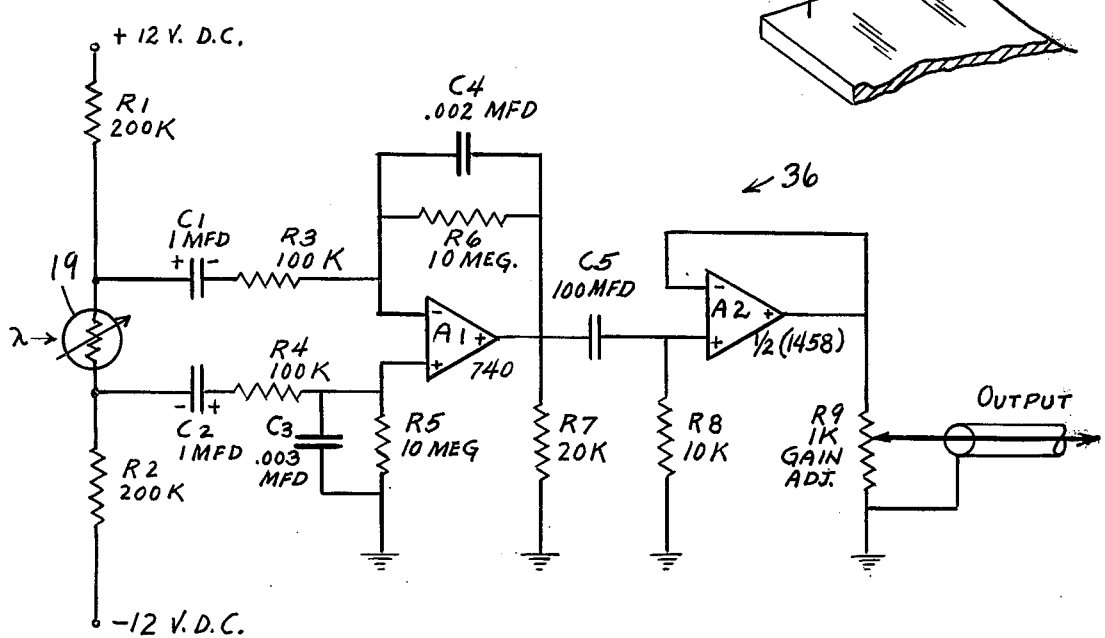
FIG. 7 is a wiring diagram of a preamplifier employed in the multifinger instrument system of FIG. 1.

FIG. 7 illustrates (omitting switching by the network 35) one typical channel of the solid state preamplifier and conditioning circuitry represented by the preamplifier units 36. The selected photodetector is shown at 19. There are four such duplicate circuits in the system represented in FIG. 1. In particular, the Clairex CL707L photodetector 19 is biased between $R_1$ and $R_2$. A Field Effect transistor (FET) input operational amplifier $A_1$ differentially measures and amplifies the voltage across the photocell. This is sensed through blocking capacitors $C_1$ and $C_2$ and $A_1$ input resistors $R_3$ and $R_4$. Resistors $R_5$ and $R_6$ establish the amplifier quiescent bias and each respectively forms a high frequency roll-off network in conjunction with $C_3$ and $C_4$. The low frequency amplifier $-3$ db point is about 1.5 Hz, and the upper $-3$ db point is about 8 Hz. The amplified signal (about 1 volt) appears at the $A_1$ output; resistor $R_7$ serves as a terminating load resistor for $A_1$. This amplified signal is then coupled to a unity gain buffer amplifier $A_2$ via $C_5$ and $R_8$. $R_8$ also establishes the quiescent bias for $A_2$ (at ground potential). Thus, virtually the same signal appears at $A_2$ input and output, except for a high to low impedance transformation allowing the signal to be driven several feet through shielded cables unaltered into the FM tape recorder and chart recorder readouts. Potentiometer $R_9$ serves as a signal gain adjustment means so as not to overload the inputs of the respective readout devices.

While a specific embodiment of an improved multifinger blood flow measuring and recording instrument has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. A multifinger blood flow measuring and recording instrument comprising a support, a plurality of open-ended finger-receiving housings mounted on said support and arranged to simultaneously individually receive all the fingers of a patient's hand, an electrical photodetector mounted in each housing, light pipe means connected to each housing opposite each photodetector and spaced therefrom to permit a finger to be inserted therebetween, a common light source optically coupled to the respective light pipe means, multichannel signal recording means, and circuit means connecting the photodetectors to the inputs of said multichannel recording means for simultaneously recording in respective channels the transmission of light from said source through a plurality of the patient's fingers.

2. The multifinger measuring and recording instrument of claim 1, and wherein said signal recording means comprises fewer than five channels and said circuit includes finger switching means for selecting the fingers whose blood flow photodetector signals are connected to the respective channels.

3. The multifinger measuring and recording instrument of claim 1, and means for individually varying the positions of said housings on said support.

4. The multifinger measuring and recording instrument of claim 1, and means for angularly individually varying the positions of said housings in a common plane on said support.

5. The multifinger measuring and recording instrument of claim 1, and means for individually varying the longitudinal and angular positions of said housings on said support.

6. The multifinger measuring and recording instrument of claim 1, and wherein the photodetectors are mounted in the bottom portions of the housings and the light pipe means extend through the top walls of the housings substantially in vertical alignment with the photodetectors.

7. The multifinger measuring and recording instrument of claim 6, and means to adjust the vertical spacing between said light pipe means and the subjacent photodetectors.

8. The multifinger measuring and recording instrument of claim 7, and wherein said vertical spacing-adjusting means comprises means to exert variable downward force on said light pipe means.

9. The multifinger measuring and recording instrument of claim 1, and wherein said support and said housings have cooperating interengaging longitudinal guide means for adjusting the longitudinal positions of the housings, and clamping means for locking the housings in longitudinally adjusted positions.

10. The multifinger measuring and recording instrument of claim 1, and wherein said support is provided with respective pivoted bracket members and said housings are slidably mounted for longitudinal adjustment on said bracket members, for adjusting the angular and longitudinal positions of said housings.

11. The multifinger measuring and recording instrument of claim 10, and cooperating locking means on the bracket members and housings for locking the housings in longitudinally adjusted positions.

12. The multifinger measuring and recording instrument of claim 11, and means for clampingly securing said bracket members in angularly adjusted positions on said support.

13. The multifinger measuring and recording instrument of claim 12, and wherein the photodetectors and light pipe means of the housings are substantially in vertical alignment, and means to individually adjust the vertical spacings between said light pipe means and photodetectors in the respective housings.

14. The multifinger measuring and recording instrument of claim 1, and wherein said circuit means includes respective preamplifiers connected between the photodetectors and said inputs of the multichannel recording means.

15. The multifinger measuring and recording instrument of claim 14, and wherein said signal recording means comprises fewer than five channels and said circuit means includes multi-position finger switching means connected between the photodetectors and preamplifiers for connecting selected photodetectors to the respective preamplifiers.

* * * * *